United States Patent
Mangold et al.

(10) Patent No.: US 6,328,944 B1
(45) Date of Patent: *Dec. 11, 2001

(54) DOPED, PYROGENICALLY PREPARED OXIDES

(75) Inventors: Helmut Mangold, Rodenbach; Rainer Golchert, Darmstadt; Stipan Katusic, Kelkheim; Karlheinz Janzon, Gelnhausen, all of (DE)

(73) Assignee: Degussa AG, Hanau (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/982,369

(22) Filed: Dec. 2, 1997

(30) Foreign Application Priority Data

Dec. 5, 1996 (DE) .............................. 196 50 500

(51) Int. Cl.⁷ .................................. C04B 35/01
(52) U.S. Cl. .................. 423/278; 423/335; 423/592; 423/606; 423/608; 423/618; 423/625
(58) Field of Search .................. 423/335, 278, 423/592, 608, 618, 606, 625

(56) References Cited

U.S. PATENT DOCUMENTS

| | | | |
|---|---|---|---|
| 3,954,945 | * 5/1976 | Lange et al. | 423/336 |
| 4,048,290 | * 9/1977 | Lee | 423/336 |
| 4,259,310 |   3/1981 | Clapper | 423/561 |
| 4,286,990 | * 9/1981 | Kleinschmitt et al. | 106/73.4 |
| 4,292,290 | * 9/1981 | Tunison, III | 423/336 |
| 4,297,143 | * 10/1981 | Kleinschmitt et al. | 501/103 |
| 4,721,530 | * 1/1988 | Ettlinger et al. | 524/243 |
| 4,937,062 | * 6/1990 | Jordan, et al. | 423/592 |

(List continued on next page.)

FOREIGN PATENT DOCUMENTS

| | | |
|---|---|---|
| 381205 | 10/1964 | (CH) . |
| 3530153 | * 3/1987 | (DE) . |
| 257443 | * 6/1988 | (DE) . |
| 19514202A | 10/1996 | (DE) . |
| 19530339 | * 2/1997 | (DE) . |
| 19619961 | * 11/1997 | (DE) . |
| 0023587A | 2/1981 | (EP) . |
| 0241647A | 10/1987 | (EP) . |
| 315169 | * 5/1989 | (EP) . |
| 0681989A1 | 11/1995 | (EP) . |
| 0703188A1 | 3/1996 | (EP) . |
| 706972 | * 4/1996 | (EP) . |
| 95381 | 9/1960 | (NL) . |

OTHER PUBLICATIONS

XP002053084, "Preparation in a Hydrogen–Oxygen Flame of Ultrafine Metal Oxide Particles", M. Formenti et al., Journal of Colloid and Interface Science, Bd. 39, Nr. 1, Apr. 1972, pp. 79–89.

Database WPI, Section CH, Derwent Publications Ltd., Class E37, AN 73–49486U, XP002053085.

WO93/14023.

(List continued on next page.)

Primary Examiner—Paul Marcantoni
(74) Attorney, Agent, or Firm—Smith, Gambrell & Russell, LLP

(57) ABSTRACT

Doped, pyrogenically prepared oxides of metals and/or non-metals which are doped with one or more doping components in an amount of 0.00001 to 20 wt. %. The doping component may be a metal and/or non-metal or an oxide and/or a salt of a metal and/or a non-metal. The BET surface area of the doped oxide may be between 5 and 600 $m^2/g$. The doped pyrogenically prepared oxides of metals and/or non-metals are prepared by adding an aerosol which contains an aqueous solution of a metal and/or non-metal to the gas mixture during the flame hydrolysis of vaporizable compounds of metals and/or non-metals.

18 Claims, 3 Drawing Sheets

U.S. PATENT DOCUMENTS

| | | | |
|---|---|---|---|
| 5,002,917 | * | 3/1991 | Deller .................................. 502/242 |
| 5,002,918 | * | 3/1991 | Deller et al. ......................... 502/263 |
| 5,015,615 | * | 5/1991 | Deller et al. ......................... 502/263 |
| 5,021,378 | * | 6/1991 | Deller et al. ........................... 502/62 |
| 5,380,687 | * | 1/1995 | Mangold et al. ................... 501/128 |
| 5,395,605 | * | 3/1995 | Billion et al. ....................... 423/339 |
| 5,424,258 | * | 6/1995 | Mangold et al. ................... 501/128 |
| 5,451,390 | * | 9/1995 | Hartmann et al. .................. 423/610 |
| 5,591,797 | * | 1/1997 | Barthel et al. ...................... 524/493 |
| 5,698,177 | * | 12/1997 | Pratsinis et al. .................... 423/613 |
| 5,858,906 | * | 1/1999 | Deller et al. ........................ 502/170 |
| 5,897,675 | * | 4/1999 | Mangold et al. ..................... 51/309 |

OTHER PUBLICATIONS

Ullmanns Encyklopadie der technischen Chemie, 4, Bd. 18, p. 653.

Ullmanns Encyklopadie der technischen Auflage 4, Bd. 21, Seite 653, pp. 464, 467, 469–471.

"Production of dispersed $SiO_2$ by hydrolysis of $SiCl_4$ in a Natural Gas Flame" Nikolina et al. vol. 4, 3–6 (1966).*

"Prepr of uniform colloidal dispersions by chemical Reactions in Aersols; Mixed Silica/titania particles" Balboa et al (1987).*

"Removal of Dust from Aersols, Containing Highly Dispersed $SiO_2$" Lyutin et al, 1969.*

* cited by examiner

DOPED, PYROGENICALLY PREPARED OXIDES

INTRODUCTION AND BACKGROUND

The present invention relates to doped, pyrogenically prepared oxides, a process for their preparation and their use.

It is known that pyrogenically prepared oxides can be coated with metal salts or metal oxides by mixing the pyrogenically prepared oxides with aqueous solutions of metal salts and then drying and/or calcining.

Products prepared in this way have the disadvantages a) that the doping substance is not homogeneously distributed in the entire primary particle or b) that, depending on the type of doping, inhomogeneities may occur during mixing. Thus, after doping and calcining, the primary particles of the doping substance may separate out and be present with much larger diameters than the primary particles of pyrogenic oxides.

It is therefore an object of the invention to achieve homogeneous doping of pyrogenically prepared oxides with another substance while at the same time avoiding problems of the prior art, and more particularly, to avoid the presence of separate primary particles of the doping substance or oxides of the doping substance alongside primary particles of the pyrogenically prepared oxide.

SUMMARY OF THE INVENTION

The above as well as other objects are obtained by the present invention in the form of doped, pyrogenically prepared oxides of metals and/or non-metals wherein the basic components are pyrogenically prepared oxides of metals and/or non-metals, prepared using flame hydrolysis techniques, which are doped with at least one doping component at 0.00001 to 20 wt. %, wherein the doping amount may preferably be in the range 1 to 10,000 ppm, and the doping component is a non-metal and/or a metal or a non-metal salt and/or a metal salt or an oxide of a metal and/or a non-metal, and the BET surface area of the doped oxides is between 5 and 600 $m^2/g$.

Another feature of the invention is a process for preparing doped, pyrogenically prepared oxides of metals and/or non-metals. In carrying out the process, an aerosol is fed into a flame, such as is used in a known manner to prepare pyrogenic oxides by flame hydrolysis and wherein this aerosol is homogeneously mixed with the gas mixture for flame oxidation or flame hydrolysis prior to reaction. The aerosol/gas mixture is allowed to react in the flame and the resulting doped pyrogenically prepared oxides are separated from the gas stream in a known manner. A salt solution or suspension which contains the components of the substance to be doped, which may be a metal salt or a non-metal salt (metalloid salt) or mixtures of both or a suspension of an insoluble metal compound or non-metal (metalloid) compound, is used as the starting material for the aerosol. The aerosol is prepared by nebulization using a two-fluid nozzle or using an aerosol generator, preferably by the ultrasonic method.

BRIEF DESCRIPTION OF THE DRAWINGS

The invention will be further understood with reference to the drawings, wherein.

DETAILED DESCRIPTION OF THE DRAWINGS

In carrying out the present invention, aerosol technology is used to feed into a flame in order to prepare pyrogenic oxides by flame hydrolysis.

Figure 1:
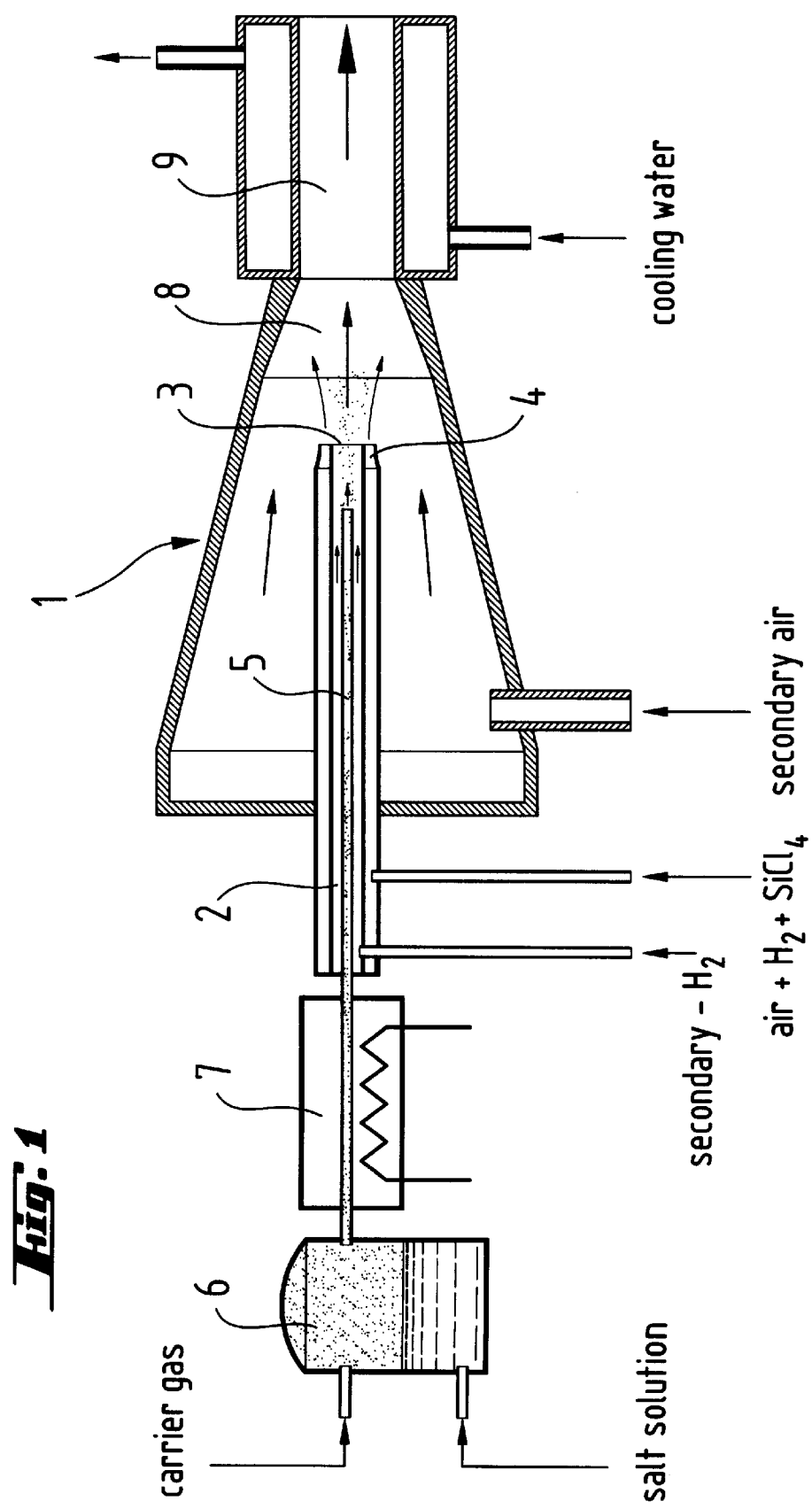
FIG. 1 is a schematic diagram of an apparatus suitable for practicing the present invention.

The aerosol may be introduced in a preferred embodiment of the invention by means of a device such as the one shown in FIG. 1. According to FIG. 1, the main part of the apparatus is a burner 1 of known construction, such as is conventionally used for preparing pyrogenic oxides. In this case, the pipes for gas and aerosol introduction may also be interchanged.

The burner 1 consists of a central tube 2 which discharges into a nozzle 3, out of which the main gas stream flows into the combustion chamber 8 and is there burned off. The inner nozzle is surrounded by the further annular nozzle 4 (mantle nozzle), out of which flows mantle- or secondary-hydrogen to prevent caking.

According to the invention, a centrally located axial tube 5 is located inside central tube 2 and terminates a few centimeters upstream of the nozzle 3 of the central tube 2. The aerosol is fed into the axial tube 5, whereby the aerosol gas stream from the axial tube 5 is homogeneously mixed with the gas stream from the central tube 2 over the last section of the central tube 2. The central tube conveys air, hydrogen and, for example, silicon tetrachloride for the pyrolysis reaction.

The aerosol is produced in an aerosol generator 6 (ultrasonic nebulizer). An aqueous salt solution 9 located in the generator 6 contains the metal or non-metal as a salt in dissolved or dispersed/suspended form and is used as the aerosol starting material. The aerosol produced by the aerosol generator 6 is passed through the heating zone 7 by means of a carrier gas stream 10, whereupon the water evaporates and small, finely distributed salt crystals remain in the gas phase. The flame pipe 11 can be cooled with cooling water 12. Secondary air can be introduced through part 13 into the chamber 8.

In a further embodiment of the invention, the aerosol may be introduced using an annular nozzle, which may be arranged at any angle, preferably at right angles, to the main gas stream.

The basic components which may be used are the non-metals/metals aluminum, niobium, titanium, tungsten, zirconium, germanium, boron and/or silicon.

The doping components which are used may be metals and/or non-metals and their compounds, provided they are soluble in or can be suspended in a liquid solution. In a preferred embodiment, compounds of transition metals and/or noble metals may be used for this purpose. The term "transition metals" is used herein in its art-recognized meaning.

By way of example, cerium and potassium salts may be used as doping components.

The flame hydrolysis process for preparing pyrogenic oxides is known from Ullmann's Encyclopedia of Industrial Chemistry, 4th ed., vol. 21, page 464, the disclosure of which is relied on and incorporated herein by reference.

Due to the fine distribution of the doping component in the aerosol, and also the high temperatures (1,000 to 2,400° C.) during subsequent flame hydrolysis, during which the doping components are possibly further reduced in size and/or melted, the doping medium is finely distributed in the gas phase during the initial stages of production of the pyrogenic oxide, so that homogeneous incorporation of the doping component in the pyrogenically prepared oxide is possible.

Using the process according to the invention, it is possible to dope all known pyrogenically prepared oxides (e.g., $SiO_2$, $TiO_2$, $Al_2O_3$, $B_2O_3$, $ZrO_2$, $GeO_2$, $WO_3$, $Nb_2O_5$) with other metal or metal oxides or non metal or non metal (metalloid) oxides or mixtures thereof.

The process according to the invention has several advantages: The aggregate or agglomerate structure of the pyrogenic oxide can be influenced by the choice of doping components. Furthermore, the pH of the pyrogenic oxide can be affected.

Catalytically active substances (e.g., cerium or noble metals) which are used as doping components can be distributed almost homogeneously in the pyrogenically prepared oxide.

Phase conversion of pyrogenically prepared oxides, for example from anatase to rutile in pyrogenically prepared titanium oxide, can be affected by doping.

Using the process according to the invention, combinations of properties of pyrogenically prepared oxides which have hitherto not been available, or available only with great difficulty, i.e. for example in processes requiring several steps, can be achieved.

Pyrogenically prepared oxides of metals and/or non-metals, doped according to the invention, can be used as fillers, as support materials, as catalytically active substances, as starting materials for preparing dispersions, as polishing materials for polishing metal or silicon wafers in the electrical industry, as ceramic substrates, in the electronics industry (CMP applications), in the cosmetics industry, as additives in the silicone and rubber industry, to adjust the rheology of liquid systems, for heat-resistant stabilization purposes, in the lacquer industry, as a heat insulation material, and the like.

The invention also provides a device for performing the process according to the invention which is characterized in that an additional tube for introducing the aerosol is arranged, preferably axially, in a burner of the structure known for preparing pyrogenic oxides, wherein the tube terminates upstream of the burner nozzle.

EXAMPLES

The burner arrangement used in examples 1 to 4 is shown schematically in FIG. 1.

Example 1 (no doping) 4.44 kg/h of $SiCl_4$ are evaporated at about 130° C. and introduced into the central tube of the burner. 3 $Nm^3$/h of primary hydrogen and 8.0 $Nm^3$/h of air are also fed to the central tube. The gas mixture flows out of the inner nozzle of the burner and burns in the combustion chamber and the water-cooled flame tube connected in series therewith. 0.5 $NM^3$/h of mantle or secondary hydrogen are fed to the mantle nozzle which surrounds the central nozzle, in order to prevent caking of the nozzle. An additional 12 $Nm^3$/h of secondary air are fed to the combustion chamber.

The aerosol flows out of the axial tube into the central tube. The aerosol consists of water vapor which has been produced in an amount of 195 g/h by ultrasonic nebulization of pure distilled water in the aerosol generator.

The nebulized water vapor is passed through a heated pipe with the assistance of a carrier gas of about 0.5 $Nm^3$/h of air, wherein the aerosol is converted into gas at a temperature of about 180° C.

At the mouth of the burner (nozzle 3), the temperature of the gas mixture ($SiCl_4$/air/hydrogen, water vapor and water aerosol) is 150° C.

The reaction gases and the resulting pyrogenic silica are passed under suction through a cooling system, by applying a reduced pressure to the flame tube, and thus cooled to about 100 to 160° C. The solid is separated from the vent gas stream in a filter or a cyclone.

The silica is produced as a white, finely divided powder. In a further step, adhering residues of hydrochloric acid are removed from the silica by treating it with water vapor-containing air at elevated temperature.

The BET surface area of the pyrogenic silica is 150 $m^2$/g.

The production parameters are given in Table 1. Further analytical data relating to the pyrogenic silica obtained are given in Table 2.

Example 2: (Doping with cerium)

The same procedure is used as described in Example 1: 4.44 kg/h of $SiCl_4$ are evaporated at about 130° C. and introduced into the central tube of the burner. 3 $Nm^3$/h of primary hydrogen and 8.0 $Nm^3$/h of air are also supplied to the central tube. The gas mixture flows out of the inner burner nozzle and burns in the combustion chamber and the water-cooled flame tube connected in series therewith. In the mantle nozzle which surrounds the central nozzle, 0.5 $Nm^3$/h of mantle or secondary hydrogen are supplied in order to prevent caking. An additional 12 $Nm^3$/h of secondary air are supplied to the combustion chamber.

The aerosol flows out of the axial tube into the central tube. The aerosol is a cerium salt aerosol which is produced in an amount of 210 g/h by ultrasonic nebulization of a 5% aqueous cerium(III) chloride solution in the aerosol generator.

The cerium salt aerosol is passed through a heated pipe with the assistance of 0.5 $Nm^3$/h of air as carrier gas, wherein the aerosol is converted into a gas and a salt crystal aerosol at temperatures around 180° C.

At the mouth of the burner, the temperature of the gas mixture ($SiCl_4$/air/hydrogen, aerosol) is 180° C.

The reaction gases and the resulting pyrogenically prepared silica, doped with cerium, are removed under suction via a cooling system by applying a reduced pressure and thus cooled to about 100 to 160° C. The solid is separated from the gas stream in a filter or cyclone.

The doped, pyrogenically prepared silica is produced as a white, finely divided powder. In a further step, adhering hydrochloric acid residues are removed from the silica by treatment with water vapor-containing air at elevated temperatures.

The BET surface area of the doped, pyrogenically prepared silica is 143 $m^2$/g.

The production parameters are given in Table 1. Further analytical data for the pyrogenic silica obtained are given in Table 2.

Example 3 (no doping) 4.44 kg/h of $SiCl_4$ are evaporated at about 130° C. and transferred to the central tube in the burner. 3 $Nm^3$/h of primary hydrogen and 8.7 $Nm^3$/h of air are also fed through the central tube. The gas mixture flows out of the inner nozzle of the burner and burns in the combustion chamber and the water-cooled flame tube connected in series therewith. In the mantle nozzle which surrounds the central nozzle, 0.5 $Nm^3$/h of mantle or secondary hydrogen are supplied in order to prevent caking. An additional 12 $Nm^3$/h of secondary air are supplied to the combustion chamber.

The aerosol flows out of the axial tube into the central tube. The aerosol consists of water vapor which is produced in an amount of 210 g/h by ultrasonic nebulization of pure distilled water in the aerosol generator.

The aerosol is passed through a heated pipe with the assistance of about 0.5 Nm³/h of air as carrier gas, wherein the aerosol is converted into a gas at temperatures around 180° C.

At the mouth of the burner, the temperature of the gas mixture (SiCl₄/air/hydrogen, water vapor or water aerosol) is 180° C.

The reaction gases and the resulting pyrogenic silica are removed under suction via a cooling system by applying a reduced pressure and thus cooled to about 100 to 160° C. The solid is separated from the gas stream in a filter or cyclone.

The silica is produced as a white, finely divided powder. In a further step, adhering hydrochloric acid residues are removed from the silica by treatment with water vapor-containing air at elevated temperature.

The BET surface area of the pyrogenic silica is 215 m²/g.

The production parameters are given in Table 1. Further analytical data for the pyrogenic silica obtained are given in Table 2.

Example 4: (Doping with cerium)

The same procedure is used as described in Example 1: 4.44 kg/h of SiCl₄ are evaporated at about 130° C. and introduced into the central tube of the burner. 3 Nm³/h of primary hydrogen and 8.7 Nm³/h of air are also supplied to the central tube. The gas mixture flows out of the inner burner nozzle and burns in the combustion chamber and the water-cooled flame tube connected in series therewith.

In the mantle nozzle which surrounds the central nozzle, 0.5 Nm³/h of mantle or secondary hydrogen are supplied in order to prevent caking.

An additional 12 Nm³/h of secondary air are supplied to the combustion chamber.

The aerosol flows out of the axial tube into the central tube. The aerosol is a cerium salt aerosol which has been produced in an amount of 205 g/h by ultrasonic nebulization of a 5% aqueous cerium(III) chloride solution in the aerosol generator.

The cerium salt aerosol is passed through a heated pipe with the assistance of 0.5 Nm³/h of air as carrier gas, wherein the aerosol is converted into a gas and a salt crystal aerosol at temperatures around 180°C.

At the mouth of the burner, the temperature of the gas mixture (SiCl₄/air/hydrogen, aerosol) is 180° C.

The reaction gases and the resulting pyrogenically prepared silica, doped with cerium, are removed under suction via a cooling system by applying a reduced pressure and thus cooled to about 100 to 160° C. The solid is separated from the gas stream in a filter or cyclone.

The doped, pyrogenic silica is produced as a white, finely divided powder. In a further step, adhering hydrochloric acid residues are removed from the pyrogenic silica by treatment with water vapor-containing air at elevated temperatures.

The BET surface area of the doped, pyrogenic silica is 217 m²/g.

The production parameters are given in Table 1. Further analytical data for the pyrogenic silica obtained are given in Table 2.

Example 5: (Doping with potassium salts)

The same procedure is used as described in Example 1, wherein a 0.5% aqueous potassium chloride solution is used as salt solution. 4.44 kg/h of SiCl₄ are evaporated at about 130° C. and introduced into the central tube of the burner. 3 Nm³/h of primary hydrogen and 8.7 Nm³/h of air are also supplied to the central tube. The gas mixture flows out of the inner burner nozzle and burns in the combustion chamber and the water-cooled flame tube connected in series therewith.

In the mantle nozzle which surrounds the central nozzle, 0.5 Nm³/h of mantle or secondary hydrogen are supplied in order to prevent caking.

The aerosol flows out of the axial tube into the central tube. The aerosol is a potassium salt aerosol which has been produced in an amount of 215 g/h by ultrasonic nebulization of a 0.5% aqueous potassium chloride solution in the aerosol generator.

The potassium salt aerosol is passed through a heated pipe with the assistance of 0.5 Nm³/h of air as carrier gas, wherein the aerosol is converted into a gas and a salt crystal aerosol at temperatures around 180° C.

At the mouth of the burner, the temperature of the gas mixture (SiCl₄/air/hydrogen, aerosol) is 180° C.

The reaction gases and the resulting pyrogenically prepared silica, doped with potassium, are removed under suction via a cooling system by applying a reduced pressure and the particle/gas stream is thus cooled to about 100 to 160° C. The solid is separated from the gas stream in a filter or cyclone.

The doped, pyrogenically prepared silica is produced as a white, finely divided powder. In a further step, adhering hydrochloric acid residues are removed from the silica by treatment with water vapor-containing air at elevated temperatures.

The BET surface area of the doped, pyrogenically prepared silica is 199 m²/g.

The production parameters are given in Table 1.

Further analytical data for the pyrogenic silica obtained are given in Table 2.

TABLE 1

EXPERIMENTAL CONDITIONS DURING THE PREPARATION OF DOPED PYROGENIC SILICAS

| No. | SiCl₄ kg/h | Prim. air Nm³/h | Sec. air Nm³/h | H₂ core Nm³/h | H₂ mantle Nm³/h | N₂ mantle Nm³/h | Gas temp. ° C. | Salt soln. | Aerosol amount kg/h | Air aeros. Nm³/h | BET m²/g |
|---|---|---|---|---|---|---|---|---|---|---|---|
| Doping with cerium salt and comparison examples | | | | | | | | | | | |
| 1 | 4.44 | 8.0 | 12 | 3 | 0.5 | 0.3 | 150 | only H₂O | 0.195 | 0.5 | 150 |
| 2 | 4.44 | 8.0 | 12 | 3 | 0.5 | 0.3 | 180 | 5% CeCl₃ | 0.210 | 0.5 | 143 |
| 3 | 4.44 | 8.7 | 12 | 3 | 0.5 | 0.3 | 180 | only H₂O | 0.210 | 0.5 | 215 |
| 4 | 4.44 | 8.7 | 12 | 3 | 0.5 | 0.3 | 180 | 5% CeCl₃ | 0.205 | 0.5 | 217 |

TABLE 1-continued
EXPERIMENTAL CONDITIONS DURING THE PREPARATION OF DOPED PYROGENIC SILICAS

| No. | $SiCl_4$ kg/h | Prim. air $Nm^3/h$ | Sec. air $Nm^3/h$ | $H_2$ core $Nm^3/h$ | $H_2$ mantle $Nm^3/h$ | $N_2$ mantle $Nm^3/h$ | Gas temp. °C. | Salt soln. | Aerosol amount kg/h | Air aeros. $Nm^3/h$ | BET $m^2/g$ |
|---|---|---|---|---|---|---|---|---|---|---|---|
| \multicolumn{12}{c}{Doping with potassium salt and comparison example} |
| 3 | 4.44 | 8.7 | 12 | 3 | 0.5 | 0.3 | 180 | only $H_2O$ | 0.210 | 0.5 | 215 |
| 5 | 4.44 | 8.7 | 12 | 3 | 0.5 | 0.3 | 180 | 0.5% KCl | 0.215 | 0.5 | 199 |

Notes:
Prim. air = amount of air in central tube; sec. air = secondary air; $H_2$ core = hydrogen in central tube; Gas temp. = gas temperature at the nozzle in the central tube; Aerosol amount = mass flow of salt solution converted into aerosol form; Air aerosol = carrier gas (air) in the aerosol.

TABLE 2
ANALYTICAL DATA FOR SAMPLES OBTAINED ACCORDING TO EXAMPLES 1 TO 5

| No. | BET [$m^2/g$] | Ce wt. µg/g | K wt. µg/g | Cl conc. ppm | LOD wt. % | LOI wt. % | Cl ppm | Grindo meter µm | Sedi- vol. vol % | Effic- iency | pH 4% sus. | Comp. b. d. g/l | Thick. Lupoda l [mPas] |
|---|---|---|---|---|---|---|---|---|---|---|---|---|---|
| \multicolumn{14}{c}{Doping with cerium salt and comparison examples} |
| 1 | 150 | — | | | 0.19 | 1.29 | | 18 | 0 | 697 | 3.98 | 27 | 1745 |
| 2 | 143 | 1860 | <5 | | 0.09 | 1.33 | | 20 | 0 | 690 | 3.93 | 26 | 1990 |
| 3 | 215 | 84 | <5 | 45 | 0.27 | 1.87 | 45 | 18 | 11 | 422 | 4.00 | 25 | 3390 |
| 4 | 217 | 2350 | <5 | 112 | 0.22 | 2.23 | 112 | 40 | 50 | 548 | 3.67 | 29 | 3680 |
| \multicolumn{14}{c}{Doping with potassium salt and comparison example} |
| 3 | 215 | | <5 | 45 | 0.27 | 1.87 | 45 | 18 | 11 | 422 | 4.00 | 25 | 3390 |
| 5 | 199 | | 300 | 55 | 0.32 | 1.86 | 55 | 60 | 50 | 451 | 4.83 | 32 | 2575 |

Notes:
Cerium content as Ce in µg/g (ppm); Potassium content as K in µg/g; LOD = loss on drying (2 h at 105° C., based on DIN/ISO 787/II, ASTM D 280, JIS K 5101/21); LOI = loss on ignition (2 h at 1000° C., based on DIN 55921, ASTM D 1208, JIS K 5101/23, with ref. to substance dried for 2 h at 105° C.); Grindometer = Grindometer value; Sedi-vol. = sediment volume; Efficiency = turbidity measurement: the method of efficiency determination (turbidity measurement) is described in Patent DE 44 00 0170; the suspension prepared by the same method is used for determining sediment volume after standing for a further 5 minutes; Compacted bulk density based on DIN/ISO 787/IX, JIS K 5101/18 (not sieved). Thickening in polyester reference system: described in EP-A 0 015 315.

Figure 2:
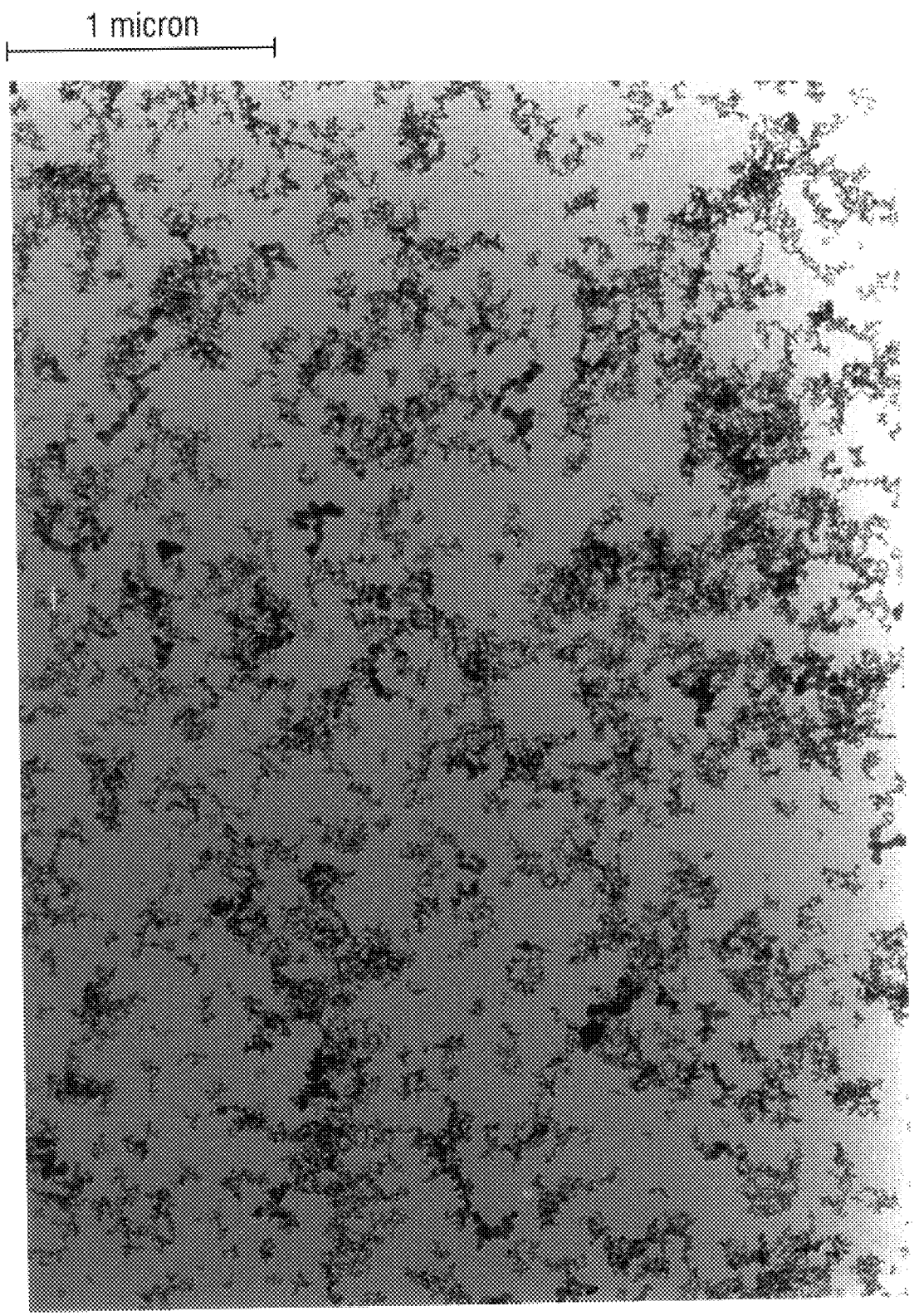
FIG. 2 is an EM photograph of pyrogenic silicon made without doping.

FIG. 2 shows an EM photograph of pyrogenic silica prepared in accordance with Example 3 (no doping).

Figure 3:
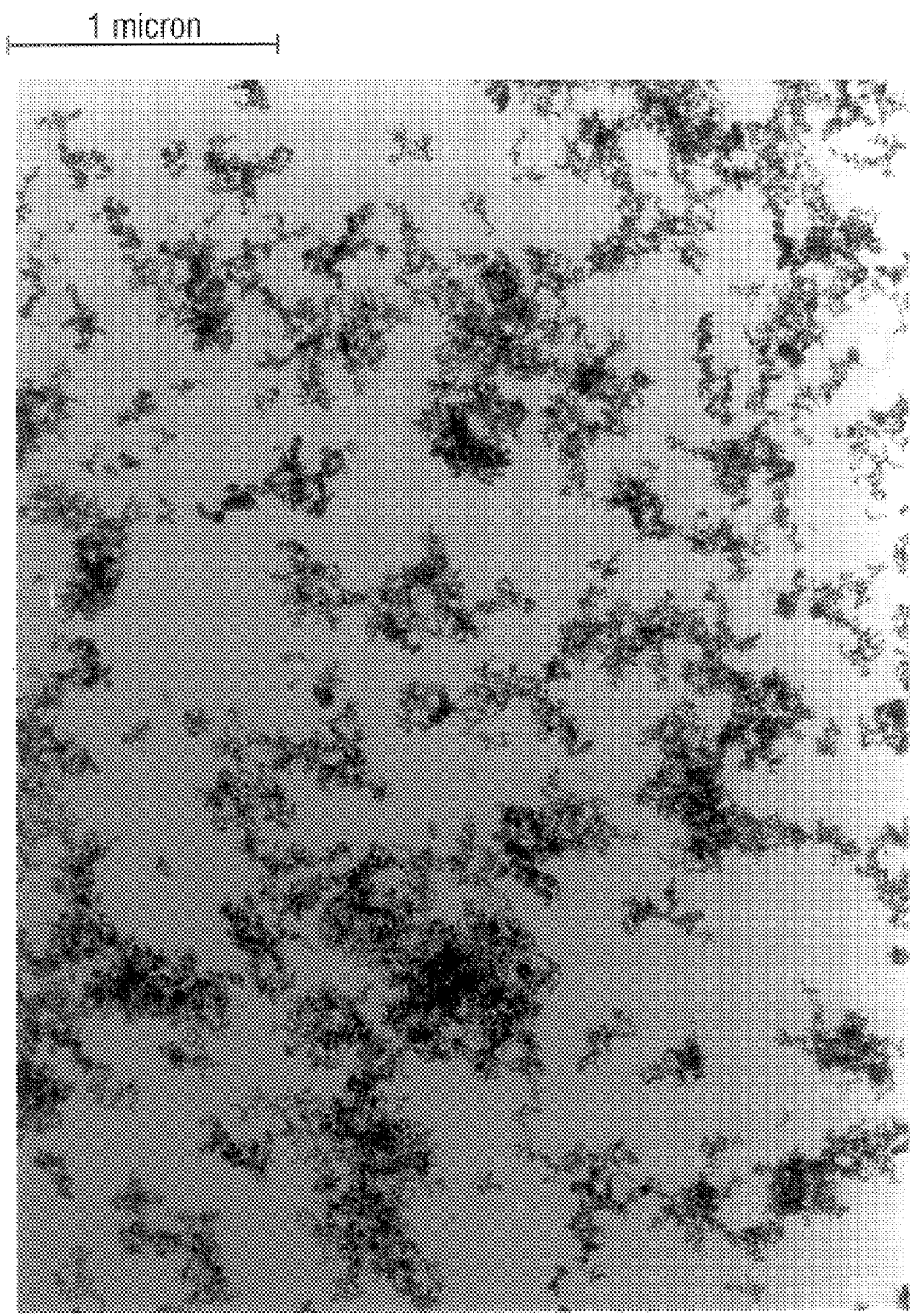
FIG. 3 is an EM photograph of pyrogenic silicon made with doping in accordance with the present invention.

FIG. 3 shows an EM photograph of pyrogenic silica prepared in accordance with Example 4 (doped with cerium salt).

It can be seen that the aggregate and agglomerate structure is modified when doped with cerium salt. Larger cohesive structures are produced with doping.

The analytical data for silica in accordance with Example 4, as compared with that for silica in accordance with Example 3, shows an increased sediment volume and a greatly increased efficiency value. This also indicates enlargement of the aggregate or agglomerate structure.

It should be noted that comparable results are obtained in accordance with the present invention when a noble metal is used in place of cerium in Example 4. Similarly, when silica is replaced with aluminum oxide, niobium oxide, germanium oxide or boron oxide, comparable results would be obtained.

Furthermore, using silica doped with cerium in accordance with the invention, a clear improvement in thickening effect is produced in unsaturated polyester resins.

Further variations and modifications will be apparent to those skilled in the art from the foregoing and are intended to be encompassed by the claims appended hereto. German priority application 195 50 500.3 is relied on and incorporated herein by reference.

What is claimed is:

1. A process of producing a doped, pyrogenic oxide which is doped using an aerosol, the process comprising:
   providing an aerosol comprised of at least one of a solution and a suspension of a
   doping substance selected from the group consisting of a metal salt, a non-metal salt, a metalloid salt, and a mixture thereof;
   conducting the aerosol through a heating zone by means of a carrier gas stream to thereby evaporate at least a portion of the aerosol;
   mixing the evaporated aerosol in the carrier gas stream with a combustible gas stream which comprises at least one of an evaporated solution and an evaporated suspension of a substance to be doped selected from the group consisting of a metal salt, a non-metal salt, a metalloid salt, and a mixture thereof, to thereby create a combustible gas stream mixture;
   reacting the combustible gas stream mixture in a flame; and
   separating the resulting doped, pyrogenic oxide from the reacted gas stream mixture.

2. The process of producing a doped, pyrogenic oxide according to claim 1, wherein the substance to be doped comprises at least one member selected from the group consisting of aluminum, niobium, titanium, tungsten, zirconium, germanium, boron and silicon.

3. The process of producing a doped, pyrogenic oxide according to claim 1 wherein the at least one of a solution and a suspension of a doping substance comprises at least one of a transition metal and a noble metal.

4. The process of producing a doped, pyrogenic oxide according to claim 1, wherein the resulting doped, pyrogenic oxide comprises at least one member selected from the group consisting of $SiO_2$, $TiO_2$, $Al_2O_3$, $B_2O_3$, $ZrO_2$, $GeO_2$, $WO_3$, and $Nb_2O_5$.

5. The process of producing a doped, pyrogenic oxide according to claim 1, wherein the at least one of a solution and a suspension of a substance to be doped comprises $SiCl_4$, and wherein the at least one of a solution and a suspension of a doping substance comprises cerium (III) chloride.

6. The process of producing a doped, pyrogenic oxide according to claim 1, wherein the process by which the doped, pyrogenic oxide is produced comprises a further step of treating the resulting doped, pyrogenic oxide with air containing water vapor.

7. The process of producing a doped, pyrogenic oxide according to claim 1, wherein the at least one of a solution and a suspension of a doping substance comprises a 5% aqueous cerium (III) chloride solution.

8. The process of producing a doped, pyrogenic oxide according to claim 1, wherein the at least one of a solution and a suspension of a doping substance comprises a 0.5% aqueous potassium chloride solution.

9. The process of producing a doped, pyrogenic oxide according to claim 1, wherein the resulting doped, pyrogenic oxide is doped with at least one doping component in an amount of from 0.00001 to 20% by weight.

10. The process of producing a doped, pyrogenic oxide according to claim 1, wherein the resulting doped, pyrogenic oxide has a BET surface area of from 5 to 600 $m^2/g$.

11. The process of producing a doped, pyrogenic oxide according to claim 1, wherein the doping component comprise at least one member selected from the group consisting of cerium, a cerium salt, and an oxide of cerium.

12. The process of producing a doped, pyrogenic oxide according to claim 1, wherein the doping component comprises at least one member selected from the group consisting of a noble metal, a noble metal salt and a noble metal oxide.

13. The process of producing a doped, pyrogenic oxide according to claim 1, wherein the doping component comprises at least one member selected from the group consisting of a transition series element, a transition series element salt and a transition series oxide.

14. The process of producing a doped, pyrogenic oxide according to claim 1, wherein the providing an aerosol is via nebulization.

15. The process of producing a doped, pyrogenic oxide according to claim 1, wherein the nebulization is ultrasonic nebulization.

16. The process of producing a doped, pyrogenic oxide according to claim 1, wherein the doping component comprises at least one of potassium, a potassium salt, and an oxide of potassium.

17. The process of producing a doped, pyrogenic oxide according to claim 1, wherein an amount of the doping substance in the resulting doped, pyrogenic oxide is from 1 to 10,000 ppm.

18. A method of modifying aggregate and agglomerate structure of pyrogenic silica doped with cerium salt, comprising:

providing a precursor of the pyrogenic silica and a precursor of the cerium salt as at least one of a solution and a suspension of the precursors; and presenting the at least one of a solution and a suspension of the precursors in aerosol form prior to a step of reacting the precursors in a flame.

* * * * *